(12) United States Patent  
Doshi et al.

(10) Patent No.: US 9,162,014 B2  
(45) Date of Patent: Oct. 20, 2015

(54) METHOD AND AN INSERTABLE MEDICAL DEVICE FOR DELIVERING ONE OR MORE PRO-HEALING AGENTS TO A TARGET SITE WITHIN A BLOOD VESSEL POST-DEPLOYMENT OF A STENT

(75) Inventors: Manish Doshi, Gujarat (IN); Divyesh Sherdiwala, Gujarat (IN); Prakash Sojitra, Gujarat (IN)

(73) Assignee: Concept Medical Research Private Limited, Surat (IN)

( * ) Notice: Subject to any disclaimer, the term of this patent is extended or adjusted under 35 U.S.C. 154(b) by 158 days.

(21) Appl. No.: 13/124,125

(22) PCT Filed: Jan. 17, 2011

(86) PCT No.: PCT/IN2011/000035  
§ 371 (c)(1),  
(2), (4) Date: Apr. 14, 2011

(87) PCT Pub. No.: WO2011/089620  
PCT Pub. Date: Jul. 28, 2011

(65) Prior Publication Data  
US 2012/0277727 A1    Nov. 1, 2012

(30) Foreign Application Priority Data

Jan. 25, 2010    (IN) .......................... 186/MUM/2010

(51) Int. Cl.

| | | |
|---|---|---|
| *A61K 9/127* | (2006.01) |
| *A61L 29/16* | (2006.01) |
| *A61L 31/16* | (2006.01) |
| *A61M 25/00* | (2006.01) |
| *A61M 25/10* | (2013.01) |
| *A61M 31/00* | (2006.01) |

(52) U.S. Cl.  
CPC ................ *A61L 31/16* (2013.01); *A61K 9/127* (2013.01); *A61L 29/16* (2013.01); *A61L 2300/22* (2013.01);  
(Continued)

(58) Field of Classification Search  
CPC  A61K 9/127; A61L 2300/22; A61L 2300/43; A61L 2300/452; A61L 2300/624; A61L 29/16; A61L 31/16; A61M 2025/0057; A61M 2025/105; A61M 31/00  
USPC .................................. 604/509, 103; 424/423  
See application file for complete search history.

(56) References Cited

U.S. PATENT DOCUMENTS 5,776,488 A * 7/1998 Mori et al. .................... 424/450  
6,383,215 B1 * 5/2002 Sass ............................. 623/1.15

(Continued)

FOREIGN PATENT DOCUMENTS

CN    1792387    6/2006  
CN    101297982    11/2008

(Continued)

OTHER PUBLICATIONS

"International Search Report dated Oct. 27, 2011", PCT Application No. PCT/IN2011/000035, 8 pages.

*Primary Examiner* — Aradhana Sasan  
(74) *Attorney, Agent, or Firm* — Timberline Patent Law Group PLLC

(57) ABSTRACT

The invention discloses an insertable medical device for delivering one or more pro-healing agents to a site of deployment of a stent in a blood vessel. The surface of the insertable medical device is coated with nano-carriers that include the one or more pro-healing agents encapsulated with one or more biological agents. The nano-carriers are released when the insertable medical device is expanded at the site. The nano-carriers thus released penetrate tissues at the site resulting in dissolution of the one or more biological agents. Thereafter, the one or more pro-healing agents are released from the nano-carriers at the site. Thus, an in-tissue release of the one or more pro-healing agents at the site is achieved thereby improving endothealization, extracellular matrix formation and healing at the site post deployment of the stent in the blood vessel.

8 Claims, 2 Drawing Sheets

(52) U.S. Cl.
CPC ........ *A61L 2300/43* (2013.01); *A61L 2300/452* (2013.01); *A61L 2300/624* (2013.01); *A61M 31/00* (2013.01); *A61M 2025/0057* (2013.01); *A61M 2025/105* (2013.01)

(56) References Cited

U.S. PATENT DOCUMENTS

2002/0022667 A1* 2/2002 Pace et al. ..................... 514/731
2005/0129727 A1* 6/2005 Weber et al. .................. 424/423
2006/0193888 A1* 8/2006 Lye et al. ...................... 424/423
2012/0164072 A1* 6/2012 Linder et al. ................. 424/1.69

FOREIGN PATENT DOCUMENTS

| | | |
|---|---|---|
| CN | 101437467 | 5/2009 |
| WO | WO 2006020742 A2 * | 2/2006 |
| WO | WO-2010140163 | 10/2010 |
| WO | WO-2010137037 | 12/2010 |

* cited by examiner

METHOD AND AN INSERTABLE MEDICAL DEVICE FOR DELIVERING ONE OR MORE PRO-HEALING AGENTS TO A TARGET SITE WITHIN A BLOOD VESSEL POST-DEPLOYMENT OF A STENT

FIELD OF THE INVENTION

The invention relates to a method and an insertable medical device for improving healing of a blood vessel post deployment of a Drug Eluting Stent (DES) in the blood vessel.

BACKGROUND OF THE INVENTION

The current methods of treating blockages in blood vessels include Percutaneous Transluminal Coronary Angioplasty (PTCA). The PTCA includes use of angioplasty balloons, Drug Eluting Stents (DESs) and Bare Metal Stents (BMSs).

In instances where the angioplasty balloons are used for treating the blockages, the inflation of the angioplasty balloons may stretch luminal layers of the blood vessel thereby resulting in inflammation at the site of treatment. The inflammation may further lead to restenosis thereby delaying healing of the blood vessel. In addition to the angioplasty balloons, the BMSs are also used post angioplasty.

The BMSs are generally covered by the tissues of the blood vessel in a timely manner. Thus, proper endothealisation may be achieved in case of the BMSs. However, because of the body's immune response to the BMSs and because of the injuries that may occur while deploying the BMSs, instances of inflammations may occur. The inflammations may eventually lead to restenosis.

As compared to the BMSs, the use of the DESs is associated with reduced instances of restenosis. However, the DESs coated on the inner surface with drugs may not allow the tissues of the blood vessel to cover the DESs thereby leading to improper endothealisation and delayed healing. Therefore, the use of the DESs is associated with problems like partial endothealisation and improper formation of extracellular matrix. The partial endothealisation and improper formation of extracellular matrix may further lead to delayed healing of the blood vessel thereby leading to unpredictable outcomes. The unpredictable outcomes may include sub-acute thrombus formation and late catch up that is not observed with the BMSs.

Additionally, the currently used DESs are coated with an anti-proliferative or immunosupressive drugs on an inner surface as well as an outer surface of the DESs. The anti-proliferative or immunosupressive drugs have the property of blocking a proliferation cell cycle of the tissues of the blood vessel. Further, the current DESs employ polymers for loading the drugs on the DESs. The use of polymers results in inflammation at the site of deployment of the DESs. The polymers also lead to complications like, improper coverage of the lesions in the blood vessel, improper release of the drug from the DESs, poor in-tissue drug release and in-tissue drug diffusion, thrombus formation, delayed healing, improper healing, focal restenosis and edge restenosis. The use of the polymers may not facilitate the tissues of the blood vessel to cover the DESs completely and in a timely manner thereby leading to poor endothealisation.

Further, because of the above-mentioned complications associated with the DESs, the patients are often prescribed with a long-term anti-platelet therapy that may extend up to the lifetime of the patient. This post-deployment drug regime has its own side effects and complications.

Therefore, there is a need in the art for an improved method for healing the blood vessels post deployment of the DESs. Further, there is need in the art for a medical device that can improve the performance of the DESs.

DETAILED DESCRIPTION OF THE INVENTION

Figure 1:
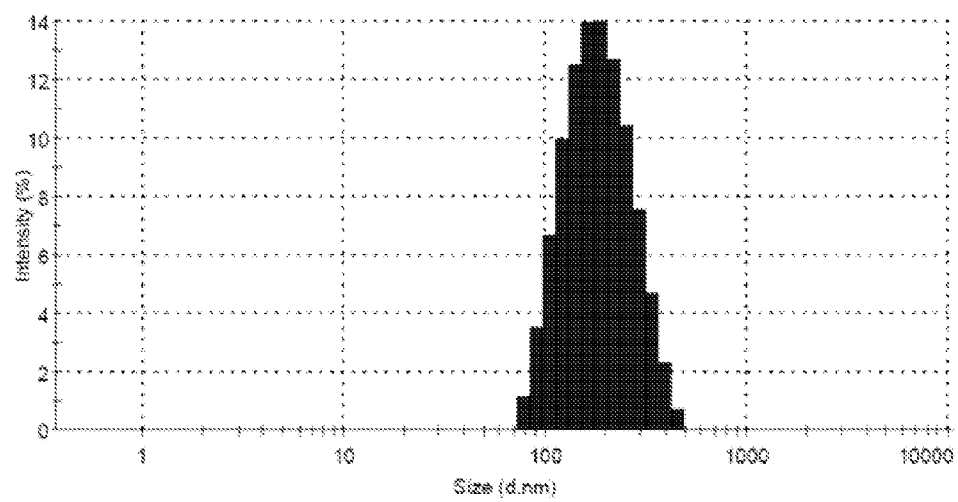
FIG. 1 illustrates size distribution of nano-particles of Lipoid E80 as detected by Malvern Zeta Sizer (ZS90) in accordance with Example 1.

Before describing in detail embodiments that are in accordance with the invention, it should be observed that the embodiments reside primarily in combinations of components of a nano-carrier eluting catheter balloon and method steps of delivering the nano-carriers for improving healing of a blood vessel post deployment of a stent. Accordingly, the components and the method steps have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, or article that comprises a list of elements that does not include only those elements but may include other elements not expressly listed or inherent to such process, method, device or apparatus. An element preceded by "comprises . . . a" does not, without more constraints, preclude the existence of additional identical elements in the process, method, device, or apparatus that comprises the element.

Further, before describing in detail embodiments that are in accordance with the invention, it should be observed that all the scientific and technical terms used in for describing the invention have same meanings as would be understood by a person skilled in the art. The terms "nano-carriers" and "plurality of nano-carriers" have the same meaning in this document unless and until specified otherwise.

Pursuant to various embodiments, the invention discloses an insertable medical device for delivering one or more pro-healing agents to a target site. The target site includes one or more of, but not limited to, a site in the blood vessel where an interventional cardiological procedure, such as, angioplasty or angiography is performed and a site in the blood vessel where a stent is deployed. The stent may include a bare metal stent, a drug-eluting stent, and any endo-luminal stent known in the art. In an embodiment, the stent includes a drug-eluting endovascular stent loaded with one or more drugs using one or more polymers.

The insertable medical device may include a catheter balloon, a diagnostic catheter, an angiography catheter, an endoscopy catheter, and any similar device. In an embodiment, the insertable medical device may be a catheter balloon. The surface of the insertable medical device is coated with a plurality of nano-carriers.

The surface includes one or more of a hydrophilic surface and a non-hydrophilic surface. The hydrophilic surface may include a layer of hydrophilic material, such as, a lubricious coating material, coated on one or more portions of the surface of the insertable medical device. Examples of the lubricious coating material include, but are not limited to, polyalkylene glycols, alkoxy polyalkylene glycols, copolymers of methylvinyl ether and maleic acid poly(vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate and at least one anti-block agent.

In an embodiment, the surface of the insertable medical device, such as, a catheter balloon has a layer of the lubricious coating material coated on one or more portions of the surface. The surface may further have one or more exposed hydrophilic surfaces. The one or more exposed hydrophilic surfaces may be created at one or more desired portions of the catheter balloon by not coating the plurality of nano-carriers on the one or more desired portions. In an embodiment, the one or more exposed hydrophilic surfaces are created at one or more of one or more portions of a distal end of the hydrophilic surface and one or more portions of a proximal end of the hydrophilic surface.

As such, the one or more exposed hydrophilic surfaces facilitate dissolution of the lubricious coating material upon coming in contact with the blood at the target site. In response to the dissolution of the lubricious coating material, the plurality of nano-carriers are released at the target site from the surface. Thus, the one or more exposed hydrophilic surfaces facilitate the release of the plurality of nano-carriers from the catheter balloon.

When the catheter balloon is inflated at the target site, about 30% to 80% of the plurality of nano-carriers are released from the surface within 15 to 90 seconds. The plurality of nano-carriers coated on one or more portions of the hydrophilic surface are released rapidly as compared to a release rate of nano-carriers from a surface of the catheter balloon devoid of a coating of the lubricious coating material. Thus, a burst release of the plurality of nano-carriers from the surface may be achieved within a short period for which the catheter balloon comes in contact with the target site. In an exemplary embodiment, about 70% to 80% of the plurality of nano-carriers are released from the surface within about 60 seconds when the catheter balloon is inflated at the target site.

Alternatively, the catheter balloon is coated with a bottom layer and a top layer. The bottom layer includes a layer of the lubricious coating material coated on the surface of the catheter balloon. The bottom layer is further covered with a top layer. The top layer includes one or more of the one or more biological agents and a polymer. Further, one or more pores are present in the top layer and plurality of nano-carriers are deposited in the one or more pores. When the catheter balloon is inflated upon coming in proximity of the target site, the plurality of nano-carriers are released from the one or more pores.

The plurality of nano-carriers includes one or more pro-healing agents encapsulated with one or more biological agents. The one or more pro-healing agents include a therapeutic agent that exhibits one or more properties of healing the tissues at the target site, promoting extracellular matrix formation at the target site, and promoting angiogenesis at the target site. The one or more pro-healing agents may include one or more of, but are not limited to, 17β-Estradiol, steroids, fatty acids, Vitamin E and analogues thereof, proteins, polypeptides, mutein, vascular endothelial growth factor (VEGF), acidic fibroblast growth factor (aFGF), basic fibroblast growth factor (bFGF), hepatocyte growth factor (j catter factor), colony stimulating factor (CSF), bioflavonoid C-Proteinase-Inhibitors, isoflavones, flavanoids, antioxidants, testeterone, progesterone, des-methyl-tocopherol, phytyl substituted chromanol, omega-3 fatty acids, DNA, RNA, dexamethasone, proanthocyanidin, catechin, epicatechin, epigallo catechin, epicatechin gallate, epigallocatechin gallate, quercetin, tannic acid, halofuginone, propyl-hydroxylase-Inhibitors, MMP-Inhibitors, batimastat, probucol, T-kase-Inhibitors, BCP 671, statins, nitric oxide donors, endothelial progenitor cell antibodies, phospholipids. In an embodiment, the one or more pro-healing agents are 17β-Estradiol.

Whereas, the one or more biological agents may include a drug carrier, an excipient, a blood component, an excipient derived from blood, a phospholipid, solid lipid nano-particles, a lipid, a vitamin and a sugar molecule. Examples of the one or more biological agents include, but are not limited to, a steroid, an estradiol, an esterified fatty acid, a non-estrefied fatty acid, glucose, inositol, L-lactate, a lipoprotein, a carbohydrate, tricalcium phosphate, precipitated calcium phosphate, substances derived from at least one of human, egg and soybean, phospholipon 80H, phospholipon 90H, Lipoid S75, Lipoid E80, Intralipid 20, Lipoid EPC, Lipoid E75, a lipid obtained from egg, a lipid obtained from soya, phosphatidylcholine, phosphatidylglycerol, phosphatidylinositol, phosphatidylserine, phosphatidic acid, cardiolipin, and phosphatidylethanolamine. In an embodiment, the one or more biological agents are Lipoid E80.

Further, the one or more biological agents exhibit one or more properties. The one or more properties may include, but are not limited to, stabilizing the one or more pro-healing agents that are present in the nano-carriers, affinity for the target site in the blood vessel, and promoting healing of the target site. Owing to the affinity of the one or more biological agents towards tissues of the target site, the nano-carriers are rapidly absorbed by the tissues of the target site as compared to absorption of nano-particles containing a drug encapsulated by a polymer. When the nano-carriers come in contact with the blood present in proximity of the tissues of the target site, the one or more biological agents are dissolved in the blood. The dissolution of the one or more biological agents results in release of the one or more pro-healing agents at the target site.

The one or more biological agents may be soluble at a pH below 7.4. Therefore, when the plurality of nano-carriers come in contact with tissues at the target site, the one or more biological agents are dissolved in the blood. The dissolution of the one or more biological agents results in release of the one or more pro-healing agents at the target site. Thus, a pH dependent release of the one or more pro-healing agents from the plurality of nano-carriers is achieved.

The nano-carriers are obtained by encapsulating the nano-crystals of the one or more pro-healing agents with the nano-particles of the one or more biological agents. As the nano-crystals of the one or more pro-healing agents are encapsulated with the nano-particles of the one or more biological agents, the surface of the nano-carriers is devoid of the one or more pro-healing agents. The nano-carriers may be coated on one or more portions of the catheter balloon when the catheter balloon is in an unfolded configuration. Alternatively, the nano-carriers may be coated on the catheter balloon when the catheter balloon is in a folded configuration.

The nano-carriers may have an average diameter ranging between 10 nm and 1200 nm. Preferably, the average diameter of the nano-carriers ranges from 300 nm to 900 nm. More preferably, the average diameter of the nano-carriers ranges from 400 nm to 600 nm. In an embodiment, the average diameter of the nano-carriers is 400 nm. Any size of the nano-carriers may be used to achieve particular therapeutic objectives, without deviating from the scope of the invention.

Alternatively, the nano-carriers may have two or more average diameters. The two or more average diameters may range from 1 nm to 5000 nm. For example, the nano-carriers may include a first set of nano-carriers with a first average diameter and a second set of nano-carriers with a second average diameter. The first average diameter is different from the second average diameter. Any number of different sets of nano-carriers with varying average diameters may be used to achieve a particular therapeutic objective without departing from the scope of the invention.

In an embodiment, the nano-carriers include a first set of nano-carriers, a second set of nano-carriers and a third set of nano-carriers. The first set of nano-carriers has a first average diameter suitable for penetrating an intima layer of the blood vessel. The second set of nano-carriers has a second average diameter suitable for penetrating a media layer through the intima layer and a vasa vasorum associated with the media layer. The third set of nano-carriers has a third diameter suitable for penetrating an adventitia layer of the blood vessel through the intima layer, the vasa vasorum associated with the media layer and a vasa vasorum associated with the adventitia layer. When the nano-carriers are released from the insertable medical device, the first set of nano-carriers penetrate the intima layer, the second set of nano-carriers penetrate the media layer through the intima layer and the vasa vasorum associated with the media layer. Whereas, the third set of nano-carriers penetrate the adventitia layer through the intima layer, the vasa vasorum associated with the media layer and the vasa vasorum associated with the adventitia layer. Thus, a size dependent penetration of the two or more nano-carriers is achieved.

The first average diameter may range from 800 nm to 1500 nm, the second average diameter may range from 300 nm to 800 nm and the third average diameter may range from 10 nm to 300 nm. The first average diameter, the second average diameter and the third average diameter may be varied to meet a particular therapeutic need without departing from the scope of the invention.

In an instance, the catheter balloon is coated with an outer layer and an inner layer of nano-carriers. The outer layer may include the third set of nano-carriers. The inner layer may include one or more of the second set of nano-carriers and the first set of nano-carriers. Further, one or more pro-healing agents present in the outer layer may be same or different from one or more pro-healing agents present in the inner layer. In accordance with various embodiments, one or more pro-healing agents present in the first set of the nano-carriers and one or more pro-healing agents present in the second set of the nano-carriers may be same or different. Also, the one or more pro-healing agents present in the second set of the nano-carriers and one or more pro-healing agents present in the third set of the nano-carriers may be same or different.

In yet another embodiment, the insertable medical device includes a set of catheter balloons. The set of catheter balloons includes a first balloon and a second balloon. The first balloon has a conical shape with a proximal diameter smaller than a distal diameter of the first balloon. The second balloon has a proximal diameter smaller than or equal to a distal diameter. Further, one or more of one or more portions of the first balloon and one or more portions of the second balloon are coated with the nano-carriers. The nano-carriers include the one or more pro-healing agents encapsulated with the one or more biological agents. The set of catheter balloons is used to deliver the one or more pro-healing agents to bifurcation lesions in a bifurcation of the blood vessel for promoting the healing of the bifurcation.

Pursuant to various embodiments, the invention also relates to a method of delivering one or more pro-healing agents to a target site using an insertable medical device coated with nano-carriers. The nano-carriers include the one or more pro-healing agents encapsulated with one or more biological agents. The method includes inserting the insertable medical device into a blood vessel and then positioning the insertable medical device at the target site. The target site includes one or more of, but not limited to, a site in the blood vessel where an angioplasty is performed and a site in the blood vessel where a stent is deployed.

Thereafter, the insertable medical device is expanded at the target site and the nano-carriers are released from the insertable medical device. The nano-carriers thus released penetrate the tissues of the target site. The one or more biological agents are dissolved when the nano-carriers penetrate the tissues of the target site thereby resulting in an in-tissue release of the one or more pro-healing agents. The insertable medical device may be inserted into the blood vessel and inflated at the target site one or more times to deliver the one or more pro-healing agents to the target site. In instances, where the target site includes a site in the blood vessel where a Drug Eluting Stent (DES) is deployed, the insertable medical device may be inflated at the target site for one or more times within few minutes to 7 days after deployment of the DES.

EXAMPLES

Example 1

Preparation of the Nano-Carriers

Lipoid E80 was obtained from Lipoid GMBH, Batch No.: 776114-1/906. 17β-Estradiol, Batch No.: 098K1372 was obtained from Sigma Aldrich (Germany). Water, other solvents and reagents used were of HPLC grade. A polyamide catheter system with COPAN Co-Polyamide dedicated angioplasty balloons for blood vessel bifurcation (hereinafter referred to as "the balloon system") coated with Hydraflow® Hydrophilic coating (hereinafter referred to as "the hydrophilic surface") was obtained from Minvasys, Paris, France.

Lipoid E80 (200 mg w/w) was dissolved in a minimum quantity of methanol, and HPLC grade water (20 ml) containing Tween80 (5 mg) was added to obtain an aqueous solution of Lipoid E80. The aqueous solution of Lipoid E80 (20 ml) was subjected to an ultrasonic homogenization for 20 to 25 minutes in an ice-cold water bath to obtain Solution A1. The Solution A1 thus obtained contained nano-particles of Lipoid E80. The solution A1 was subsequently analyzed for particle size detection using Malvern Zeta Sizer (ZS90) [Malvern, UK] size detector. FIG. 1 illustrates the size distribution of nano-particles of Lipoid E80 as detected by Malvern Zeta Sizer (ZS90). The z-average diameter of the nano-particles of the Lipoid E80 was found to be 174 nm.

17β-Estradiol (20 mg w/w) was dissolved in 5 ml methanol, and then 100 ml of HPLC grade water was added to obtain an aqueous solution of 17β-Estradiol by recrystallization. The aqueous solution of 17β-Estradiol (100 ml) was subjected to an ultrasonic homogenization for 100 to 200 minutes in an ice-cold water bath to obtain Solution A2. The Solution A2 thus obtained contained nano-crystals of 17β-Estradiol.

Figure 2:
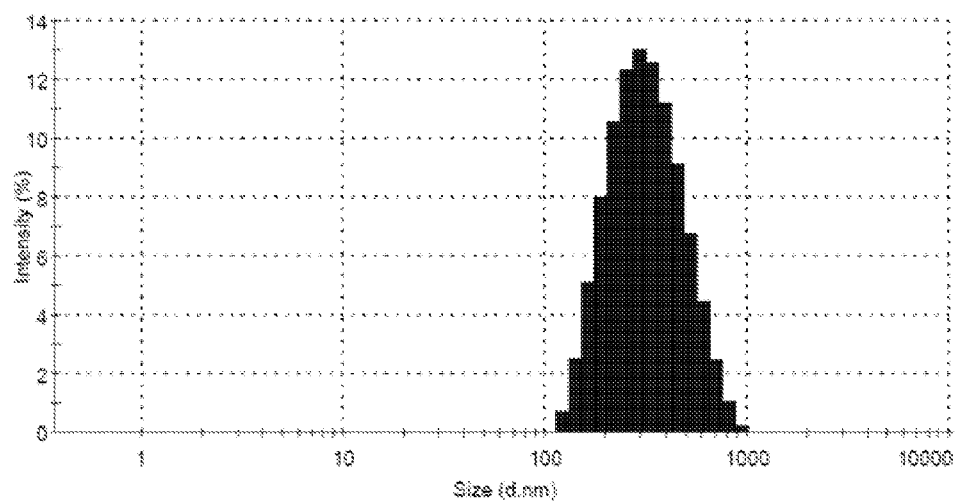
FIG. 2 illustrates the size distribution of nano-carriers as detected by Malvern Zeta Sizer (ZS90) in accordance with Example 1.

After 100 to 180 minutes, 10 ml of Solution A1 was added to Solution A2 drop by drop using a 5 ml pipette with the ultrasonic homogenization process to obtain Solution A3. Solution A3 was then subjected to an ultrasonic homogenization process for another 15 minutes after complete addition. Thereafter, Solution A3 was kept in an ultrasonic cleaner water bath (PCI) for 20 minutes. Solution A3 thus obtained contained nano-carriers (nano-crystals of 17β-Estradiol surrounded by nano-particles of Lipoid E80). Solution A3 was subsequently analyzed for particle size detection using Malvern Zeta Sizer (ZS90) [Malvern, UK] size detector. FIG. 2 illustrates the size distribution of nano-carriers as detected by Malvern Zeta Sizer (ZS90). The z-average diameters of nano-carriers were found to be 283 nm.

Solution A3 (Aqueous solution of nano-carriers) was further subjected to extraction with dichloromethane. Solution A3 (about 100 ml) was transferred to a 250 ml separating funnel. 50 ml of dichloromethane was added to the 250 ml separating funnel. The resultant mixture was then shaken for 15 minutes and allowed to stand. Thereafter, two layers i.e., an aqueous layer and a dichloromethane layer were observed in the 100 ml separating funnel. The dichloromethane layer was separated from the aqueous layer. The dichloromethane layer was further evaporated to get a concentrated solution. The dichloromethane layer was evaporated to a volume of 25 ml. The concentrated solution i.e., a solution of nano-carriers was allowed to cool at room temperature and was stored in an amber colored small measuring flask with batch number. Subsequently, the solution of the nano-carriers was used for coating the balloon system.

Example 2

Preparation of the Drug Delivery System

The Balloon System

The solution of the nano-carriers (5 ml) was fed into the reservoir of a coating machine. The balloons of the balloon system were mounted on a rotating mandrel of the coating machine one by one. Each balloon of the balloon system was exposed to an atomization nozzle of the coating machine separately. The balloon system was rotated at 5 to 40 rpm by rotating the mandrel and simultaneously the solution of nano-carriers was sprayed over the balloons at 0.5 to 4.0 psi inert gas pressure and in two oscillations. Thus, the balloons coated with the nano-carriers (hereinafter referred to as "the coated balloon system") was obtained. The coated balloon system was then removed and checked under a high-resolution microscope for the coating surface smoothness and presence of any foreign particles.

Various embodiments of the invention provide a method and an insertable medical device for improving healing of a blood vessel post deployment of a BMS or a DES in the blood vessel. Further, the invention provides an insertable medical device for improving endothealisation and extracellular matrix formation at a site of deployment of a stent. The insertable medical device promotes the post deployment healing of the blood vessel. The insertable medical device also reduces instances of complications like acute thrombus formation, sub-acute thrombus formation, and late thrombus formation that are likely to follow the deployment of stents.

Those skilled in the art will realize that the above-recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made to the invention without deviating from the scope of the invention. Accordingly, the specification is to be regarded in an illustrative rather than a restrictive sense, and all such modifications are intended to be included within the scope of the invention.

What is claimed is:

1. An insertable medical device for delivering a 17β-estradiol pro-healing agent to tissues in proximity with a stent deployed in a blood vessel, the insertable medical device comprising:
   a catheter balloon;
   a surface of the catheter balloon;
   a plurality of nano-carriers coated on the surface, each nano-carrier of the plurality of nano-carriers of a size within a range between approximately 100 nanometers and approximately 1000 nanometers and including at least one nano-particle of the 17β-estradiol pro-healing agent surrounded by individual nano-particles of a biological agent LIPOID E80 egg lecithin mixture, each nano-particle of the biological agent LIPOID E80 egg lecithin mixture of a size within a range between approximately 70 nanometers and approximately 500 nanometers, wherein the plurality of nano-carriers are released from the catheter balloon to the tissues in response to expanding the catheter balloon at the tissues, wherein the plurality of nano-carriers upon releasing from the catheter balloon penetrate the tissues leading to dissolution of the nano-particles of the biological agent LIPOID E80 egg lecithin mixture and subsequent release of the 17β-estradiol pro-healing agent in the tissues;
   wherein the surface is on the catheter balloon and comprises a layer of a hydrophilic lubricious coating material coated on one or more portions of the surface, the surface further comprising one or more exposed hydrophilic lubricious surfaces, the one or more exposed hydrophilic lubricious surfaces created at one or more portions of the catheter balloon by not coating each exposed hydrophilic lubricious surface with the plurality of nano-carriers on the one or more portions of a distal end of the hydrophilic lubricious surface and one or more portions of a proximal end of the hydrophilic lubricious surface;
   the surface further comprising one or more underlying hydrophilic lubricious surfaces between the nano-carriers and the catheter balloon; and
   wherein the exposed hydrophilic lubricious surfaces dissolve rapidly when exposed to the tissues thereby exposing a part of the one or more underlying hydrophilic lubricious surfaces to the tissues causing a rapid release of approximately 70% to 80% of the nano-carries from the catheter balloon within approximately 60 seconds when the catheter balloon is inflated.

2. The insertable medical device of claim 1, wherein the plurality of nano-carriers comprise a first set of nano-carriers having a first average diameter and a second set of nano-carriers having a second average diameter, wherein the first average diameter is different from the second average diameter.

3. The insertable medical device of claim 2, wherein the first average diameter ranges between 100 nm to 700 nm and the second average diameter ranges from 300 nm to 1000 nm.

4. The insertable medical device of claim 1, wherein the plurality of nano-carriers comprise a first set of nano-carriers with a first average diameter, a second set of nano-carriers with a second average diameter, and a third set of nano-carriers with a third average diameter.

5. The insertable medical device of claim 4, wherein the first average diameter ranges between 100 nm to 500 nm, the second average diameter ranges from 300 nm to 800 nm, and the third average diameter ranges from 500 nm to 1000 nm.

6. A method for delivering a 17β-estradiol pro-healing agent to tissues in proximity with a stent deployed in a blood vessel, the method comprising:

positioning an insertable catheter balloon at the tissues, the insertable catheter balloon comprising a surface coated with a plurality of nano-carriers, each nano-carrier in a size range between approximately 100 nanometers and approximately 1000 nanometers, a nano-carrier of the plurality of nano-carriers comprising at least one nano-particle of the 17β-estradiol pro-healing agent surrounded by individual nano-particles of a biological agent LIPOID E80 egg lecithin mixture in a size range between approximately 70 nanometers and approximately 500 nanometers;

wherein the surface is on the catheter balloon and comprises a layer of a hydrophilic lubricious coating material coated on one or more portions of the surface, the surface further comprising one or more exposed hydrophilic lubricious surfaces, the one or more exposed hydrophilic lubricious surfaces created at one or more portions of the catheter balloon by not coating each exposed hydrophilic lubricious surface with the plurality of nano-carriers on the one or more portions of a distal end of the hydrophilic lubricious surface and one or more portions of a proximal end of the hydrophilic lubricious surface;

the surface further comprising one or more underlying hydrophilic lubricious surfaces between the nano-carriers and the catheter balloon;

wherein the exposed hydrophilic lubricious surfaces dissolve rapidly when exposed to the tissues thereby exposing a part of the one or more underlying hydrophilic lubricious surfaces to the tissues causing a rapid release of approximately 70% to 80% of the nano-carries from the catheter balloon within approximately 60 seconds when the catheter balloon is inflated; and expanding the insertable catheter balloon at the tissues, wherein the plurality of nano-carriers are released from the insertable catheter balloon in response to expanding the insertable catheter balloon, whereby the plurality of nano-carriers upon releasing from the insertable catheter balloon penetrate the tissues leading to dissolution of the nano-particles of the biological agent LIPOID E80 egg lecithin mixture and subsequent release of the 17β-estradiol pro-healing agent in the tissues.

7. The method of claim 6, wherein positioning and expanding of the insertable catheter balloon at the tissues are repeated at a predetermined interval to deliver the 17β-estradiol pro-healing agent to the tissues.

8. The method of claim 7, wherein the predetermined interval ranges from one day to 30 days.

* * * * *